United States Patent [19]

Uchikawa et al.

[11] Patent Number: 4,673,910
[45] Date of Patent: Jun. 16, 1987

[54] MOISTURE SENSITIVE ELEMENT CONTAINING HIGH TEMPERATURE DECOMPOSITION RESIDUE OF ORGANO-SILICON POLYMER AS SENSITIVE ELEMENT

[75] Inventors: Fusaoki Uchikawa; Morihisa Takeuchi; Kōzō Shimamoto; Kunihiko Miyao; Kimio Momiyama; Hisao Watarai, all of Kanagawa, Japan

[73] Assignee: Mitsubishi Denki Kabushiki Kaisha, Tokyo, Japan

[21] Appl. No.: 432,953

[22] PCT Filed: Dec. 25, 1981

[86] PCT No.: PCT/JP81/00410

§ 371 Date: Sep. 29, 1982

§ 102(e) Date: Sep. 29, 1982

[87] PCT Pub. No.: WO83/01339

PCT Pub. Date: Apr. 14, 1983

[30] Foreign Application Priority Data

Sep. 30, 1981 [JP] Japan ............................ 56-155961
Sep. 30, 1981 [JP] Japan ............................ 56-155962

[51] Int. Cl.⁴ .................... H01C 7/00; G01N 27/12
[52] U.S. Cl. .................................. 338/35; 73/336.5
[58] Field of Search ............... 338/35, 34; 73/335, 73/336.5

[56] References Cited

U.S. PATENT DOCUMENTS

| | | | |
|---|---|---|---|
| 3,864,659 | 2/1975 | Furuuchi et al. | 338/35 |
| 3,983,527 | 9/1976 | Ohsato et al. | 73/336.5 X |
| 4,142,400 | 3/1979 | Colla et al. | 338/34 X |
| 4,236,307 | 12/1980 | Colla et al. | 29/857 |
| 4,378,691 | 4/1983 | Terada et al. | 338/35 X |
| 4,386,336 | 5/1983 | Kinomoto et al. | 338/35 |

FOREIGN PATENT DOCUMENTS

| | | | |
|---|---|---|---|
| 55-6186 | 2/1980 | Japan | 338/35 |
| 56-126756 | 5/1981 | Japan . | |
| 2025068 | 1/1980 | United Kingdom . | |
| 2071323 | 9/1981 | United Kingdom | 338/34 |

Primary Examiner—Roy N. Envall, Jr.
Assistant Examiner—C. N. Sears
Attorney, Agent, or Firm—Oblon, Fisher, Spivak, McClelland & Maier

[57] ABSTRACT

A moisture sensitive element having on an insulating substrate a moisture sensitive section that changes its electrical resistance according to the humidity of atmosphere. The moisture sensitive section is prepared by mixing a polymerized organic silicon compound with particles of a moisture sensitive, electrically resistant material, applying a coat of the resulting blend onto the insulating substrate, and sintering the coat. The element is strong, has good moisture sensitivity characteristics and can be used for an extended period with little decrease in the moisture sensitivity and little change in the value of resistance.

9 Claims, 17 Drawing Figures

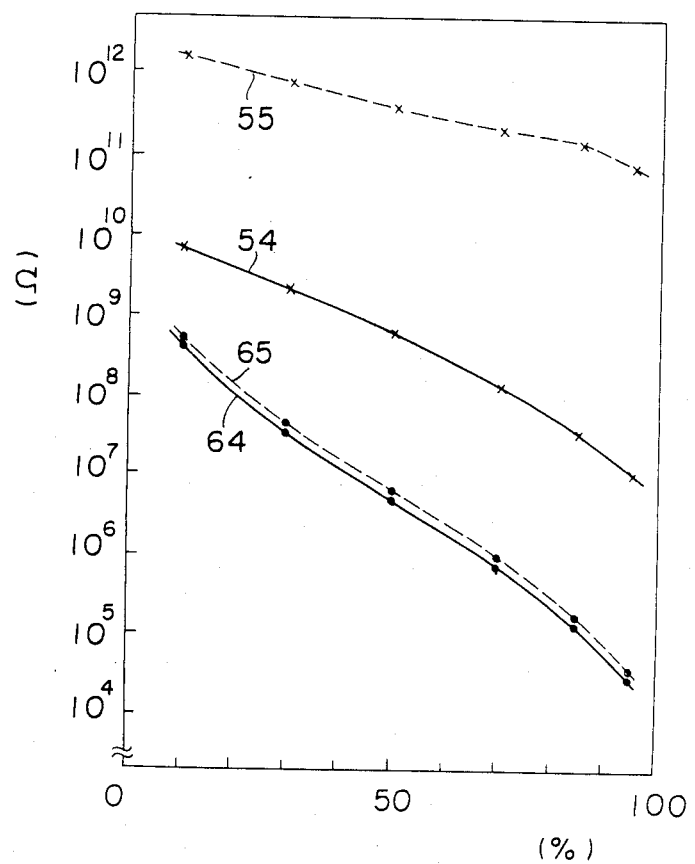
F I G. 14

4,673,910

MOISTURE SENSITIVE ELEMENT CONTAINING HIGH TEMPERATURE DECOMPOSITION RESIDUE OF ORGANO-SILICON POLYMER AS SENSITIVE ELEMENT

FIELD OF TECHNOLOGY

The present invention relates to a moisture sensitive element that is designed to detect the humidity of atmosphere by using the change in electrical resistance of the moisture sensitive section of the element.

BACKGROUND OF TECHNOLOGY

Heretofore, the moisture sensitive section of the element that has the capability described above has been made of an electrolyte such as lithium chloride or calcium chloride, a vapor-deposited film of a semiconductor such as selenium or germanium, as well as a metal oxide or metal oxide ceramic using aluminum oxide, titanium oxide or iron oxide.

Among these materials, the electrolyte has so much hygroscopicity in the high-humidity region that is becomes fluid and has low strength, with the result that the measurable moisture range is from 0 to about 60% rh. The vapor-deposited semiconductor film needs vacuum deposition and is not easy to fabricate, and in addition, the humidity reading is affected by temperature. The metal oxide is stable both physically and chemically and provides a strong element, but it generally needs a firing temperature of 1000° C. or more which often reduces the area of the moisture sensitive surface. Therefore, the conventional moisture sensitive sections prepared from either of the above mentioned materials have their own defect and are not satisfactory.

SUMMARY OF THE INVENTION

The present invention has been developed to eliminate the above defects of the conventional techniques and one of its objects is to provide a moisture sensitive element having a moisture sensitive section that has high sensitivity to detect humidity, is capable of measuring a wide range of humidity, can be made from a cheap and easily available material, can be fabricated easily and which yet provides a strong element.

In the conventional ceramic moisture sensitive element, the metal and oxygen atoms are ionized by being charged positively and negatively to some extent, so if a static electrical field is applied, as by d.c. current, to the element, the two ions are polarized in opposite directions to change (increase) the electrical resistance of the element. To prevent this, it has been necessary to use an a.c. current that unavoidably needs a more complex detection circuit than when a d.c. current is used. Therefore, another object of the present invention is to provide a moisture detecting element that is capable of detecting humidity on d.c. current.

Still another object of the present invention is to provide a moisture sensitive element operable with d.c. current that uses a moisture sensitive section that contains 10 to 95 wt.% of a polymerized organic silicon compound, 5 to 90 wt.% of an amorphous silica powder and 0 to 30 wt.% of another additive component and which is sintered at a temperature of 300° C. or higher.

A further object of the present invention is to provide a moisture sensitive element operable with d.c. current that uses a moisture sensitive section made of a sintered product containing 20 to 85 wt.% of a polymerized organic silicon compound, 0.5 to 15 wt.% of a carbonaceous powder and 5 to 60 wt.% of a siliceous powder.

BRIEF DESCRIPTION OF THE DRAWINGS

FIG. 14 is a graph showing the time-dependent relative humidity vs. logarithmic electrical resistance characteristics of a conventional moisture sensitive element and the element of the seventh example;

PREFERRED EMBODIMENT OF THE INVENTION

The present invention is hereunder described in great detail. According to the present invention the moisture sensitive section is made of a material which uses as a binder component the decomposition residue that is obtained by decomposing thermally a composition primarily made of a polymerized organic silicon compound (silicone) such as silicon resins, silicone grease or silicone oil, and particles of an inorganic powder that has moisture sensitivity and is stable both physically and chemically are dispersed uniformly throughout this binder. The material of the moisture sensitive section is first described by taking up silicon resins as an example of the binder. The structure of silicon resins is such that hydrocarbon groups are attached to side chains from the siloxane bond —Si—O—Si—O—. Upon heating, the hydrocarbon groups in side chains are decomposed gradually to form a hard solid residue that is made of said siloxane bond and decomposed hydrocarbon groups. At higher firing temperature, the decomposition of the hydrocarbon groups is accelerated and the surface of said solid residue becomes porous. As a result, the material contained within the solid residue comes to show on the surface. Therefore, in the present invention, the moisture sensitive section is made of tiny particles of a moisture sensitive, electrically resistant material, and the invention is based on the finding that a strong film of said particles bound to each other by the thermal decomposition residue of the polymerized organic silicon compound exhibits a great change in electrical resistance according to the change in the ambient humidity (from 0 to 100% r.h.). The moisture sensitive section according to the present invention can be made of a particulate material having a large effective area of the moisture sensitive surface, and in addition, the material need be fired at lower temperatures than conventional metal oxides (ceramics) and can provide a fairly strong moisture sensitive element.

The first example of the present invention is now described.

EXAMPLE 1

Figure 1:
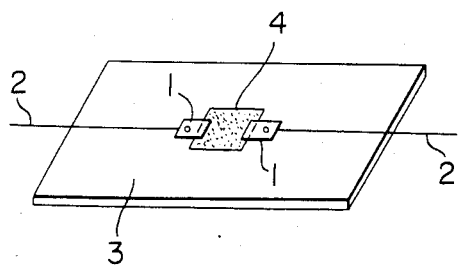
FIG. 1 is a perspective view of a moisture sensitive element according to a first example of the present invention.
Figure 2:
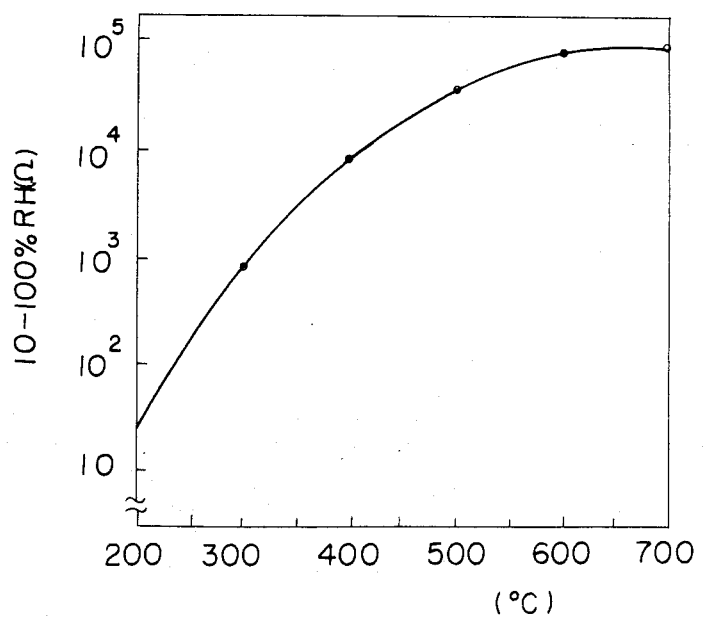
FIG. 2 is a curve graph showing the firing temperature vs. electrical resistance characteristics of the moisture sensitive element of the present invention.
Figure 3:
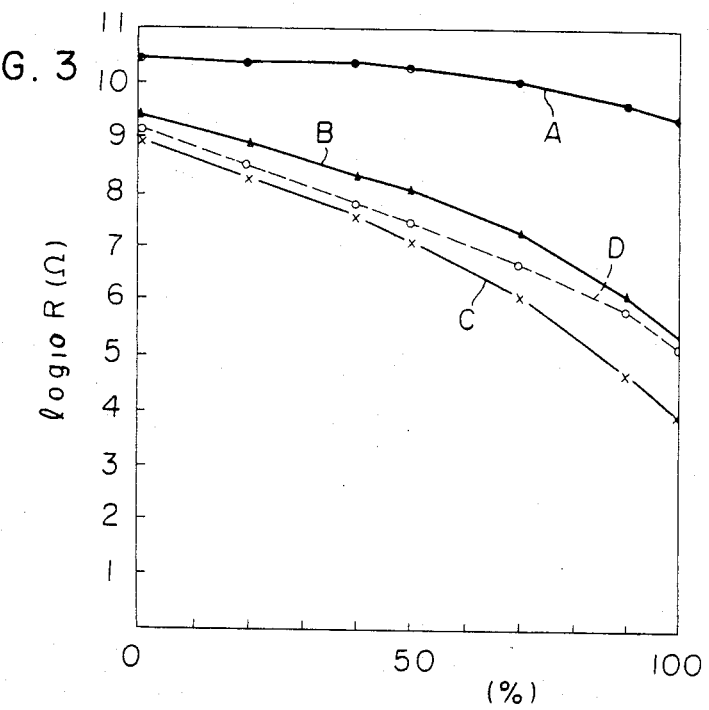
FIGS. 3, 4 and 5 are graphs showing the relative humidity vs. logarithmic electrical resistance characteristics of the first to third examples.

Silicone varnish having a silicon resin (methylphenyl silicone) dissolved in xylene was used as the starting material for binder, and a blend prepared by mixing the varnish under stirring with $TiO_2$ (i.e. moisture sensitive, electrically resistant material) twice the weight of the varnish was applied to a plurality of alumina insulating substrates to form a film about 200μ thick and 5 mm square on each substrate. The so formed films were fired at temperature that varied from 200° to 700° C. by 100° C. To each of the films, a pair of gold (Au) electrodes (1) were attached, as shown in the embodiment of FIG. 1, by vapor deposition, and a conductor wire (2) was bonded to each electrode (1). In FIG. 1, the numeral (3) indicates the substrate and (4), the moisture sensitive section made of the fired film. The moisture sensitive section (4) was exposed to air whose relative humidity was changed from 0 to 100%, and the electrical resistance of the moisture sensitive section (4) at the respective humidities was measured. FIG. 2 shows the change in the electrical resistance of the moisture sensitive element in the range of from 0 to 100% r.h. according to various firing temperatures. As is clear from FIG. 2, the higher the firing temperature, the greater the change in the resistance in the range of from 0 to 100% r.h., and the moisture sensitive section exhibits desired characteristics for use in the moisture sensitive element. FIG. 3 shows the relation between the relative humidity and logarithmic resistance at firing temperature of 200°, 400° and 600° C. In FIG. 3, curves (A), (B) and (C) show the moisture sensitivity characteristics of the moisture sensitive section at the firing temperatures of 200°, 400° and 600° C., respectively. It is also clear from FIG. 3 that the higher firing temperatures provide better moisture sensitivity characteristics. But as FIG. 2 indicates, the moisture sensitivity has a tendency to be saturated when the firing temperature exceeds 600° C. Curve (D) shows the moisture sensitivity characteristics of a conventional ceramic (sintered $TiO_2$) humidity sensor that were measured under the same conditions.

These characteristics are understandable since the fired component of the silicon resin used as the binder is presumed to undergo the following change depending upon the heating temperature:

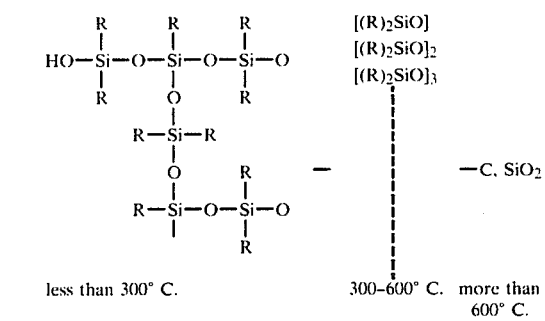

wherein
R: methyl group or phenyl group,
C: carbon atom.

Microscopic observation of the moisture sensitive section exposed to various firing temperatures showed that as the firing temperature increased from 300° C., the silicone decomposed and the surface of the sensitive section became porous, and that as the surface became more porous, the moisture sensitive material came to show on the surface to achieve increased moisture sensitivity. FIG. 3 clearly shows that the humidity sensor of the present invention is provided with even better moisture sensitivity characteristics than the conventional product by increasing the firing temperature.

The second example of the present invention is now described.

EXAMPLE 2

Figure 4:
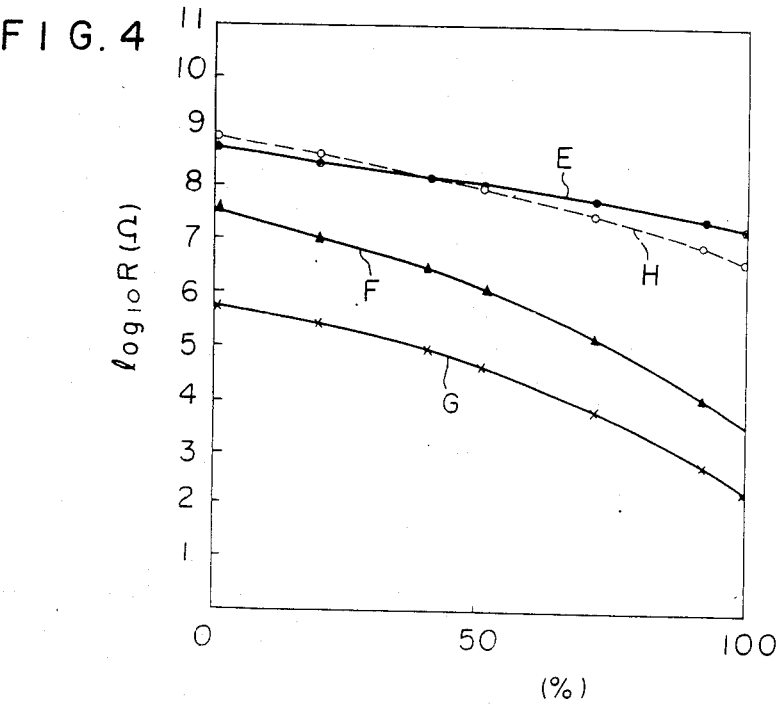

A binder entirely the same as in Example 1 was used. A blend was prepared as in Example 1 by mixing the binder under stirring with ZnO powder (moisture sensitive material) about 1.5 times the weight of the binder. Like FIG. 3, FIG. 4 shows the relation between the relative humidity and logarithmic resistance at firing temperatures of 200°, 400° and 600° C. The same characteristics were measured for a comparative humidity sensor having the conventional ZnO ceramic moisture sensitive section. In FIG. 4, curves (E), (F) and (G) show the characteristics of the moisture sensitive section at the firing temperatures of 200°, 400° and 600° C., respectively. Curve (H) shows the same characteristics of the conventional moisture sensitive section.

EXAMPLE 3

Figure 5:
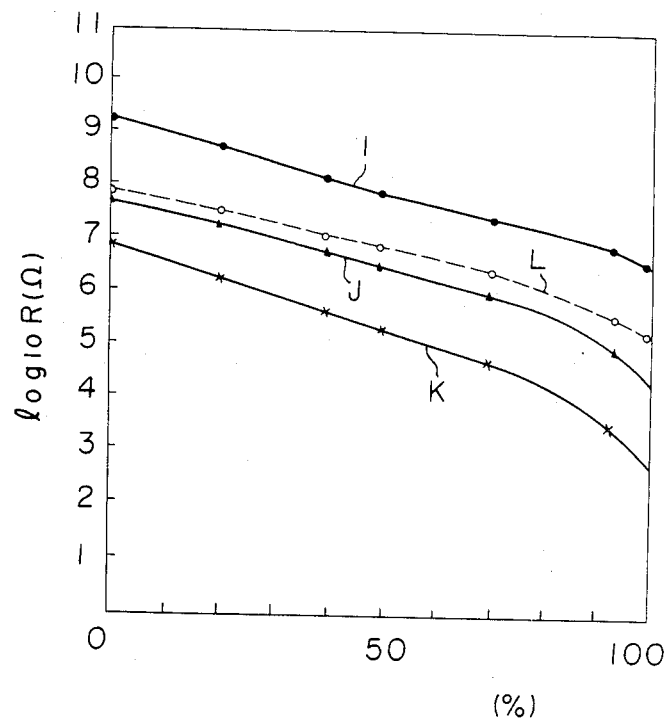

Silicone varnish having methyl silicone dissolved in a mixed solvent of toluene and xylene was used as the binder, and a blend was prepared as in Example 1 by mixing the binder under stirring with $Cr_2O_3$ powder (moisture sensitive material) about twice the weight of the binder. Like FIG. 3, FIG. 5 shows the relation between the relative humidity and logarithmic resistance at firing temperatures of 200°, 400° and 600° C. Again, the same characteristics were measured for a comparative humidity sensor having the conventional $Cr_2O_3$ ceramic moisture sensitive section. In FIG. 5, curves (I), (J) and (K) show the characteristics of the moisture sensitive section at the firing temperatures of 200°, 400° and 600° C., respectively. Curve (L) shows the same characteristics of the conventional moisture sensitive section.

As is clear from FIGS. 4 and 5, the higher the firing temperature, the more sensitive to moisture the humidity sensor of the present invention is in comparison with the conventional product.

According to the present invention, the methyl-phenyl silicone and methyl silicone used as the binder in the above examples can be replaced with other silicon resins, modified type silicon resins such as epoxy-modified silicone, and polymerized organic silicon compounds such as silicone oil and silicone rubber so long as they are decomposition residues obtained by thermally decomposing compositions primarily made of materials generally referred to as silicone. Experiments have revealed that these decomposition residues have substantially the same moisture sensitivity characteristics as those of the methyl-phenyl silicone and methyl silicone.

According to the present invention, $TiO_2$, ZnO and $Cr_2O_3$ used as the moisture sensitive material in Examples 1 to 3 may be replaced with any particulate inorganic material such as metal oxides (e.g. $Fe_2O_3$, $Al_2O_3$ and CuO), powders of composite metal oxides or metal oxide ceramics, metal powders such as Se and Ge, as well as mixtures thereof. The present inventors have confirmed by experiments that these particulate moisture sensitive materials have better moisture sensitivity characteristics than the conventional vapor-deposited film or sintered product because of their large effective area of the moisture sensitive surface.

The moisture sensitive element of the present invention was subjected to cyclic humidity measurement; it was found to be an extremely stable element whose characteristics changed in a range of from only 2 to 3%, and its response speed was sufficiently high to meet the practical requirements, i.e. it took only a few seconds to follow a change in relative humidity from 0% to 100%.

Another advantage of the moisture sensitive element of the present invention is that as higher firing temperatures are employed to manufacture the element, the binder serving as the backbone becomes more inorganic to provide greater strength and higher physical and chemical stability. The firing temperature need not be higher than about 600° C. for achieving the objects of the present invention. This means yet another advantage in that the moisture sensitive element of the present invention can be produced by firing at lower temperatures than the metal oxide (ceramic) product that is the most practical of the conventional moisture sensitive elements and which must be produced at a firing temperature of at least about 800° C., usually at least 1000° C.

The fourth example of the present invention relates to a moisture sensitive element that can be operated with d.c. current to detect humidity.

In the conventional ceramic moisture sensitive element, the metal and oxygen atoms are ionized by being charged positively and negatively to some extent, so if a static electrical field is applied, as by d.c. current, to the element, the two ions are polarized in opposite directions to change (increase) the electrical resistance of the element. To prevent this, it has been necessary to use an a.c. current that unavoidably needs a more complex detector circuit than when a d.c. current is used. This problem is solved by the present invention and a moisture sensitive element that can be operated on d.c. current is provided.

As a result of studies on various moisture sensitive materials, the present inventors have found that the above defect of the conventional ceramic moisture sensitive element can be eliminated by a material prepared by sintering at 300° C. or higher a composition containing a polymerized organic silicon compound and amorphous silica powder whose sum is at least 70% of the total weight of the composition. The moisture sensitive element of the present invention has the following advantages: it can be manufactured by firing at low temperatures; it is stable both physically and chemically; it has high strength and good moisture sensitivity characteristics; it can be used over an extended period without experiencing a substantial change in the electrical resistance and moisture sensitivity characteristics; even if these values are changed, the initial good performance can be restored by heating at much lower temperatures than have been required conventionally; and the element can be operated on d.c. current.

Details of the present invention are now described by the following examples.

EXAMPLE 4

Comb electrodes of Pt-Pd alloy paste were formed on an alumina insulating substrate by screen printing, and after a Pt lead was bonded to each electrode, the entire assembly was baked. A thinner was added to a composition having formulation 1 indicated below, and the mixture was stirred with a stirrer, and the previously prepared assembly was dipped in the blend to form a coat in a thickness of about 60 μm. Following preliminary firing at 80° C. for 10 minutes, the coat was fired at 600° C. for 30 minutes to cure and sinter it. The result was a moisture sensitive element of the present invention as shown in FIG. 6, wherein (11) indicates the insulating substrate, (12) is each electrode, (13) is the moisture sensitive section (coat) and (14) is each lead.

| (Formulation 1) | | |
|---|---|---|
| Polymerized organic silicon compound: | Methyl silicone prepolymer Expoxy-modified silicone prepolymer | 53 wt. % |
| Amorphous silica powder: | Silica glass | 38 wt. % |
| Additives: | Organic titanium compound, drying oil, bentonite | 9 wt. % |

The additives in formulation 1 were used for such purposes as accelerated crosslinking (curing) and drying of the coat, prevention of cracking and improved bonding properties. To achieve the same purposes, suitable materials are to be added to other formulations given in the following description.

Figure 6:
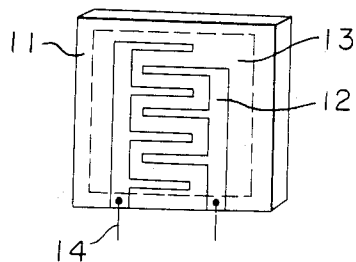
FIG. 6 is a perspective view of a moisture sensitive element according to a fourth example of the present invention.
Figure 7:
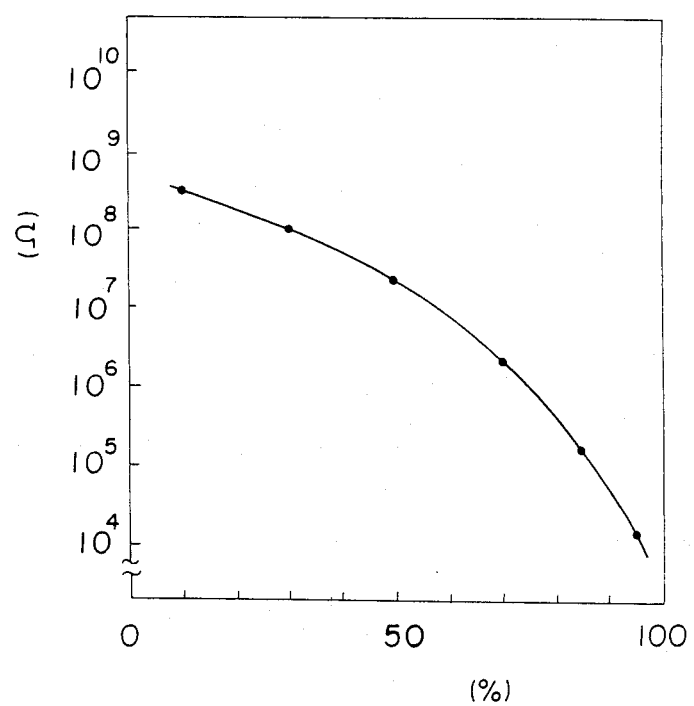
FIG. 7 is a graph showing the relative humidity vs. logarithmic electrical resistance characteristics of the moisture sensitive element according to the fourth example.
Figure 8:
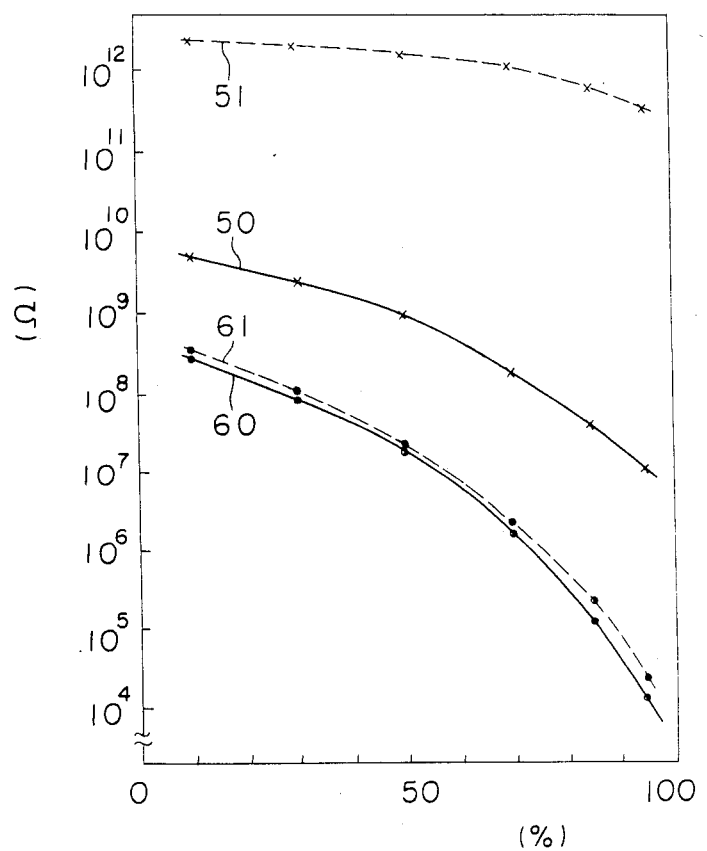
FIG. 8 is a graph showing the time-dependent relative humidity vs. logarithmic electrical resistance characteristics of a conventional moisture sensitive element and the element of the fourth example.

Two samples, the moisture sensitive element of the present invention prepared as above and a conventional ceramic moisture sensitive element wherein the moisture sensitive section was made of $Al_2O_3$—MgO—$TiO_2$ ceramic sintered at 1250° C. for 5 hours and the other components were the same as shown in FIG. 6, were subjected to the measurement of their moisture sensitivity characteristics and time-dependent change thereof. First, a d.c. voltage of 1.5 V was applied to each element to measure the value of resistance; as soon as the voltage was applied, the resistance of the conventional type increased to cause marked polarization, but this phenomenon was entirely absent from the element of the present invention which exhibited a gradual change in resistance and was capable of measuring the change in resistance with d.c. current in the range of from low to high humidities. The result is shown in FIG. 7. To compare the moisture sensitivity characteristics of the two elements, an a.c. (50 Hz) voltage of 1.5 V was applied and the change in resistance due to varying relative humidities and its time-dependent change were measured. The results are shown in FIG. 8. Curve (50) shows the initial moisture sensitivity characteristics of the conventional type and curve (51) shows the same characteristics after storage at room temperature for 80 days. Curve (60) shows the initial moisture sensitivity characteristics of the element of the present invention and curve (61) shows the same characteristics after storage at room temperature for 80 days. As is clear from FIG. 8, the resistance of the conventional moisture sensitive element was about one hundred times as large as the original value after storage for 80 days and accordingly, the moisture sensitivity decreased significantly, but the resistance of the moisture sensitive element of the present invention increased only a little upon storage for 80 days and no decrease in the moisture sensitivity occurred. As indicated by the initial moisture sensitivity characteristic curves (50) and (60), the element of the present invention had values of resistance at least one tenth of those of the conventional type, and at, say, a relative humidity of 60-70%, the resistance is on the order of $10^6$ ohms, and this helps provide a detector circuit easy to use. The two elements that had been stored for 80 days and which had the characteristics shown by curves (51) and (61) were put in an electric furnace where they were heated from 150° C. by 50° C., and at each testing temperature, the samples were heated for 10 minutes to check the temperature at which the decreased moisture sensitivity characteristics were restored to the respective initial values on curves (50) and (60). The characteristics of the conventional sample were not restored to its initial characteristics unless it was heated to higher than 600° C., whereas the sample of the present invention was regenerated to the initial characteristics completely upon heating at 200° C. These results show that even after cyclic adsorption and desorption of water vapor (moisture), OH is not as firmly bonded to the element of the present invention as the conventional element, and even if OH bonding occurs, the element of the present invention can be regenerated by heating at temperatures considerably lower than have been required for the conventional type.

Review is now made as to the reason why the element according to the fourth example of the present invention can be operated on d.c. current unlike the conventional ceramic moisture sensitive element and why it has a long service life by withstanding the bonding of OH groups. X-ray diffractiometry of the fired product of polymerized organic silicon compound that is the primary component of the moisture sensitive section of the element of the present invention showed that at temperatures higher than 300° C. where the organic components (e.g. methyl and phenyl groups) start to decompose and to be lost by burning, amorphous $SiO_2$ is the primary component.

It was also found that in this temperature range, the organic components that remain after burning and decomposition and a trace amount of carbon are dispersed in the fired product. In the moisture sensitive element of the present invention, the amorphous material which is the primary component and the presence of residual carbon contribute to increased electron conductivity and inhibited ionic conductivity, and there is little likelihood that ion polarization will occur in a static electrical field, and this is probably the reason why the element of the present invention can be used with d.c. current. The probable reason for the high resistance of the element of the present invention to OH bonding is that first of all, the amorphous material is the primary component and secondly, at firing temperature higher than 300° C., a composite material made of the combination of the organic matter which remains after decomposition of the polymerized organic silicon compound and the inorganic matter (amorphous silica) is inherently incapable of causing strong chemical adsorption of water vapor (moisture) or OH groups on the surface of the moisture sensitive section.

EXAMPLE 5

A thinner was added to a comparison having formulation 2 indicated below, and the mixture was stirred with a stirrer. The blend was applied in a thickness of about 45 μm with a brush to an alumina substrate having electrodes formed of the same material as used in Example 4, and after preliminary firing at 80° C. for 20 minutes, the assembly was fired at 400° C. for 20 minutes to cure and sinter the coat. The result was a moisture sensitive element of the present invention as shown in FIG. 9, wherein (21) is the insulation substrate, (22) is each electrode, (23) is the moisture sensitive section, (24) is each lead, (25) is a heater, and (26) is a pair of leads to the heater.

| (Formulation 2) | | |
| --- | --- | --- |
| Polymerized organic silicon compound: | Methylphenyl silicone prepolymer | 75 wt. % |
| Amorphous silica powder: | Ethyl silicate polymer, Aerosil | 13 wt. % |
| Additives: | Organoaluminum compound, MgO and frit | 12 wt. % |

Formulations 1 and 2, as well as the formulations indicated below contain a thinner that dissolved the polymerized organic silicon compound and helped mixing with the other components and improve applicability of coat, and this thinner is a mixture of toluene, xylene, diacetone alcohol and butyl cellosolve.

Figure 9:
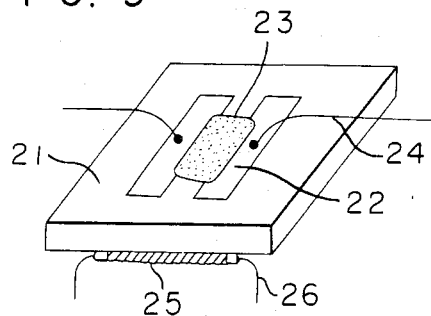
FIG. 9 is a perspective view of a moisture sensitive element according to a fifth example of the present invention.
Figure 10:
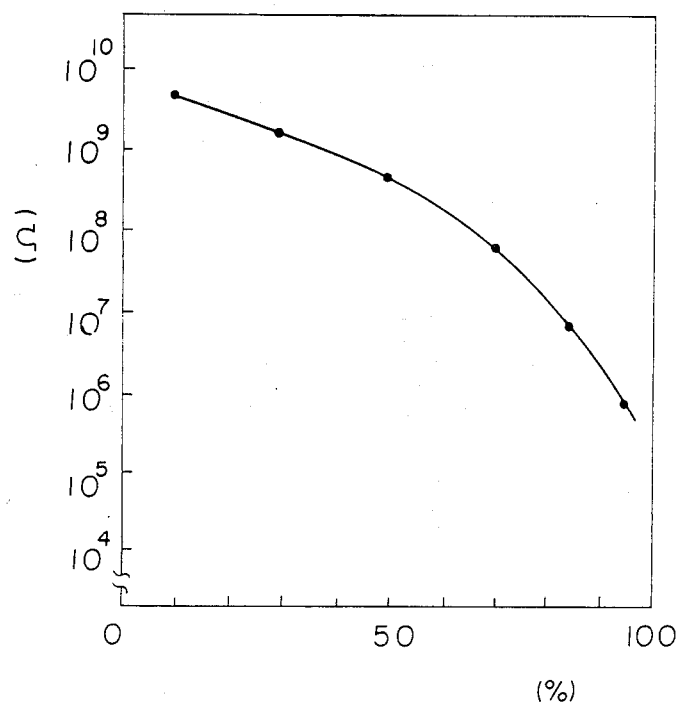
FIG. 10 is a graph showing the relative humidity vs. logarithmic electrical resistance characteristics of the moisture sensitive element according to the fifth example.

Two samples, the moisture sensitive element of the present invention prepared as above and a conventional ceramic sensitive element wherein the moisture sensitive section was made of $Cr_2O_3$—CaO ceramic sintered at 1200° C. for 6 hours and the other components were the same as shown in FIG. 9, were subjected to the measurement of their moisture sensitivity characteristics and time-dependent change thereof. First, a d.c. voltage of 1.5 V was applied to each element as in Example 4; as soon as the voltage was applied, the resistance of the conventional type made of $Cr_2O_3$—CaO ceramic increased to cause marked polarization. This phenomenon was more conspicuous as the fired element was left in air for a longer period. This is probably because as the adsorption of moisture in air proceeds, more of the atoms that make up the ceramic are ionized to accelerate the polarization. On the other hand, the element of the present invention fabricated as described above was entirely free of polarization upon application of d.c. current, and instead, it exhibited a gradual change in resistance and was capable of measuring the change in resistance with d.c. current in the range of from low to high humidities as shown in FIG. 10.

Figure 11:
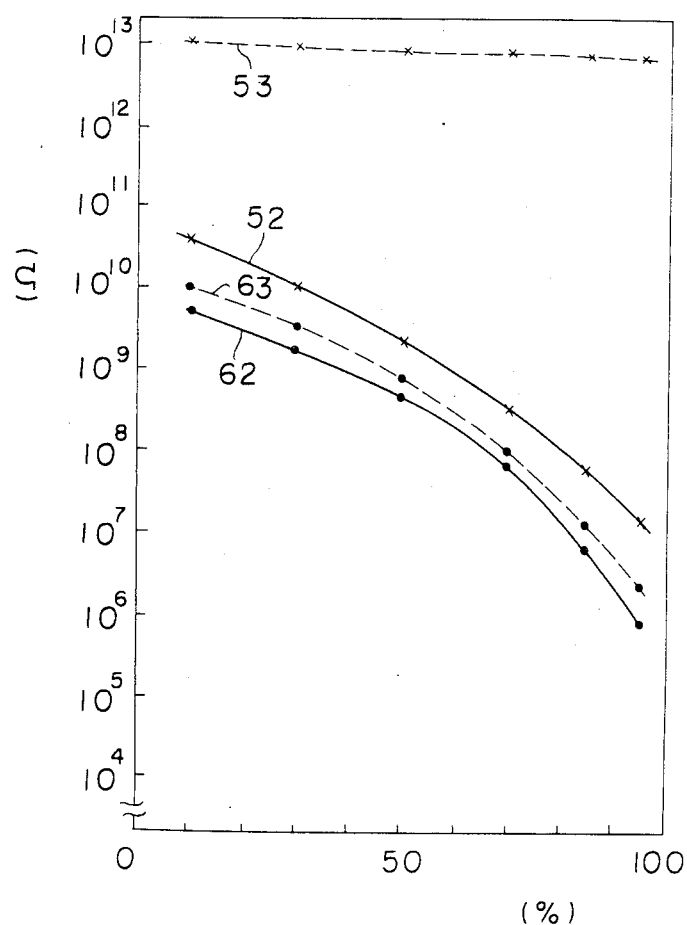
FIG. 11 is a graph showing the time-dependent relative humidity vs. logarithmic electrical resistance characteristics of a conventional moisture sensitive element and the element of the fifth example.

Then, the moisture sensitivity characteristics of the two elements and their time-dependent change were examined by applying an a.c. voltage of 1.5 V to the elements. To accelerate the time-dependent deterioration, the two elements were immersed in boiling water for 2 hours, and the resulting moisture sensitivity characteristics were measured for comparison with the initial characteristics. The results are shown in FIG. 11. In FIG. 11, curve (52) indicates the initial characteristics of the conventional type and curve (53) indicates the characteristics after the accelerated deterioration test, whereas curve (62) indicates the initial characteristics of the element of the present invention and curve (63) indicates the characteristics after the accelerated deterioration test. It can be seen from FIG. 11 that the values of resistance of the conventional type that had been subjected to the accelerated deterioration test were at least one hundred times as large as the initial values and its moisture sensitivity was lost completely, whereas the moisture sensitivity of the element of the present invention that had been subjected to the accelerated deterioration test was little decreased although its resistance was somewhat increased. This means the immersion in boiling water to accelerate the time-dependent deterioration was a testing method so severe so to deprive the conventional element of its ability to detect humidity, but the element of the present invention withstood this test and little deterioration occurred, so it can be said to have very high resistance to time-dependent deterioration. The element of the present invention also proved to be very strong since no signs of deterioration such as blisters or cracks were found in the moisture sensitive coat even after the test.

The probable reasons for the decrease in the initial characteristics of the conventional element in the above described accelerated deterioration test are primarily the strong chemical adsorption (bonding) of OH groups and the subsequent clogging of pores (reduction in the effective area of the moisture sensitive surface) due to the expansion of the volume of the particles in the microstructure of the ceramic. Following the accelerated deterioration test, a current was applied to the heater (see FIG. 9) on the two elements exhibiting the characteristics of curves (53) and (63) to increase their temperature from 150° C. by 50° C., and at each testing temperature, the samples were heated for 15 minutes to check the temperature at which the decreased moisture sensitivity characteristics were restored to the respective initial values on curves (52) and (62). As in Example 4, the characteristics of the conventional sample were not restored to its initial characteristics unless it was heated to higher than 600° C., whereas the sample of the present invention was regenerated to the initial characteristics completely upon heating at 250° C. which is mucn lower than is required for the conventional sample.

EXAMPLE 6

Moisture sensitive elements of the present invention having the constructions described in FIGS. 6 and 9 were fabricated as in Examples 4 and 5 using compositions having formulations 3 and 4 indicated below, and their moisture sensitivity characteristics and the time-dependent change thereof were checked upon application of d.c. and a.c. currents. As a result, it turned out that, as in Examples 4 and 5, the moisture sensitive elements of the present invention could be operated with d.c. current and experienced little time-dependent deterioration due to bonding of OH groups. The two samples were subjected to a boiling water immersion test as in Example 5 and were found to have great strength since their moisture sensitive coat did not deteriorate at all.

| (Formulation 3) | | |
| --- | --- | --- |
| Polymerized organic silicon compound: | Methylphenyl silicon prepolymer | 75 wt. % |
| Amorphous silica powder: | Silica glass, colloidal silica, silica | 52 wt. % |
| Additives: | Metal soap, mica powder, TiO₂ | 15 wt. % |
| (Formulation 4) | | |
| Polymerized organic silicon compound: | Methylphenyl silicone and acryl-modified silicone prepolymer | 70 wt. % |
| Amorphous silica powder: | Silica glass, Aerosil | 25 wt. % |
| Additives: | Organic titanium compound, asbestos powder | 5 wt. % |

As described in the previous examples, the present inventors fabricated mositure sensitive elements using various polymerized organic silicon compounds, amorphous silica powders and various additives and by varying the proportions of the respective components, and checked their moisture sensitivity characteristics, the time-dependent change thereof and the properties of the cost in the moisture sensitive section (e.g. strength of bond to the substrate), and found that the proportions of the components must be within the following ranges:

| Polymerized organic silicon compound: | 10–95 wt. % |
| --- | --- |
| Amorphous silica powder: | 5–90 wt. % |
| Other additives: | 0–30 wt. % |

The sum of the polymerized silicon compound and amorphous silica powder must be at least 70% of the total weight. If their sum is less than 70%, the good characteristics superior to those of the conventional type element as described in the examples are not obtained. As already mentioned, the firing temperature of the element must be higher than 300° C. because it is necessary that the primary component of the moisture sensitive section of the element of the present invention be essentially amorphous $SiO_2$.

As effected in the examples, the element of the present invention can be fabricated with ease and advantage by forming the moisture sensitive section in the form of a film applied from the specified composition onto an insulating substrate.

According to the present invention, prepolymers of various silicon resins (including modified types) of the types described in the examples can be used as the polymerized organic silicon compound, and, for example, commercial silicone varnish (prepolymers of methylphenyl silicone, etc. dissolved in solvents such as toluene and xylene) can be used with ease. As for the amorphous silica powder, any powder of the type described in the examples that is primarily made of "uncrystallized" silica can be used. The initial form of the amorphous silica need not be a powder, but in the fabrication of a moisture sensitive element, it is mixed with other components and turns into a powder eventually.

The seventh example of the present invention relates to another embodiment of the moisture sensitive element that can be operated with d.c. current.

This example discovered by the present inventors uses a moisture sensitive section made of a sintered product containing 20 to 85 wt.% of a polymerized organic silicon compound, 0.5 to 15 wt.% of a carbonaceous powder and 5 to 60 wt.% of a silicic powder.

Such moisture sensitive element of the present invention has the following advantages: it can be manufactured by firing at low temperatures; it is stable both physically and chemically; it has high strength and good moisture sensitivity characteristics; it can be used over an extended period without experiencing a substantial change in the electrical resistance and moisture sensitivity characteristics; even if these values are changed, the initial good performance can be restored by heating at much lower temperatures than are usually required for the conventional product; and the element can be operated on d.c. current.

Details of the present invention are now described by the following examples.

EXAMPLE 7

Comb electrodes of Pt-Pd alloy paste were formed on an aluminum insulating substrate by screen printing, and after a Pt lead was bonded to each electrode, the entire assembly was baked. A thinner was added to a composition having formulation 5 indicated below, and the mixture was stirred with a stirrer, and the previously prepared assembly was dipped in the blend to form a coat in a thickness of about 50 μm. Following preliminary firing at 80° C. for 20 minutes, the coat was fired at 550° C. for 30 minutes to cure and sinter it. The result was a moisture sensitive element of the present invention as shown in FIG. 12, wherein (31) indicates the insulating substrate, (32) is each electrode, (33) is the moisture sensitive section (coat) and (34) is each lead.

| (Formulation 5) | | |
|---|---|---|
| Polymerized organic silicon compound: | Methylphenyl silicone prepolymer | 54 wt. % |
| Carbonaceous powder: | Carbon black | 3 wt. % |
| Silicic powder: | Silica, Aerosil | 35 wt. % |
| Additives: | Organic titanium compound, drying oil, talc | 8 wt. % |

The additives in formulation 5 were used for such purposes as accelerated crosslinking (curing) and drying of the coat, prevention of cracking and improved bonding properties. To achieve the same purposes, suitable materials are to be added to other formulations given in the following description.

Figure 12:
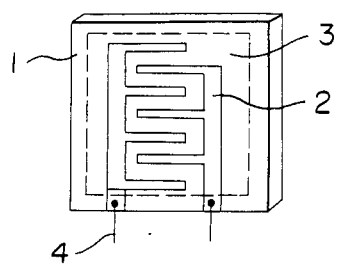
FIG. 12 is a perspective view of a moisture sensitive element according to a seventh example of the present invention.
Figure 13:
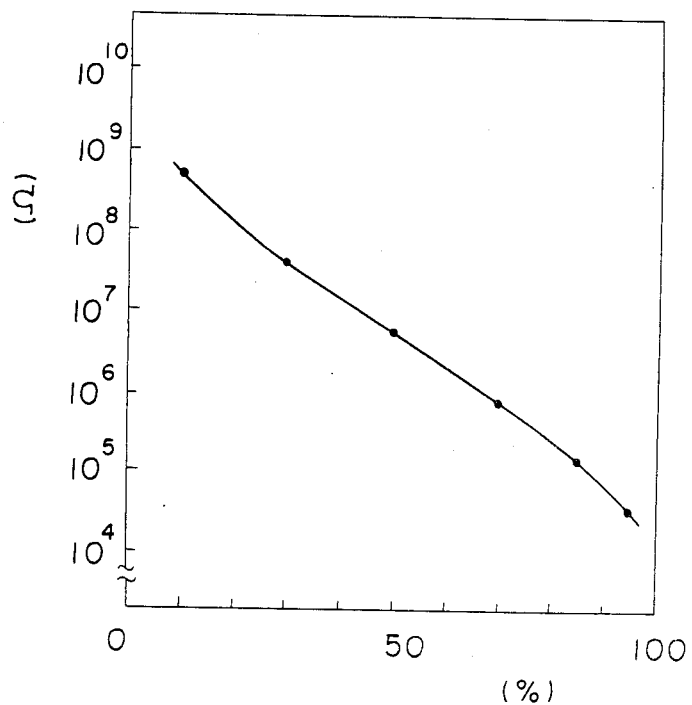
FIG. 13 is a graph showing the relative humidity vs. logarithmic electrical resistance characteristics of the moisture sensitive element according to the seventh example.

Two samples, the moisture sensitive element of the present invention prepared as described above and a conventional ceramic moisture sensitive element wherein the moisture sensitive section was made of $Al_2O_3$—$MgO$ ceramic sintered at 1300° C. for 5 hours and the other components were the same as shown in FIG. 12, were subjected to the measurement of their moisture sensitivity characteristics and time-dependent change thereof. First, a d.c. voltage of 1 V was applied to each element to measure the value of resistance; as soon as the voltage was applied, the resistance of the conventional type increased to cause marked polarization, but this phenomenon was entirely absent from the element of the present invention which exhibited a gradual change in resistance and was capable of measuring the change in resistance upon d.c. current in the range of from low to high humidities. The result is shown in FIG. 13. To compare the moisture sensitivity characteristics of the two elements, an a.c. (50 Hz) voltage of 1 V was applied and the change in resistance due to varying relative humidities and its time-dependent change were measured. The results are shown in FIG. 14. Curve (54) shows the moisture sensitivity characteristics of the conventional type and curve (55) shows the same characteristics after storage at room temperature for 60 days. Curve (64) shows the initial moisture sensitivity characteristics of the element of the present invention and curve (65) shows the same characteristics after storage at room temperature for 60 days. As is clear from FIG. 14, the resistance of the conventional moisture sensitive element was about one hundred times as large as the original value after storage for 60 days, and accordingly, the moisture sensitivity decreased significantly, but the resistance of the moisture sensitive element of the present invention increased only a little upon storage for 60 days and no decrease in moisture sensitivity occurred. As indicated by the initial moisture sensitivity characteristic curves (54) and (64), the element of the present invention had values of resistance at least one tenth of those of the conventional type, and at, say, a relative humidity of 60–70%, the resistance is on the order of $10^6$ ohms, and this helps provide a detector circuit easy to use.

The two elements that had been stored for 60 days and which had the characteristics shown by curves (55) and (65) were put in an electric furnace where they were heated from 150° C. by 50° C., and at each testing temperature, the samples were heated for 10 minutes to check the temperature at which the decreased moisture sensitivity characteristics were restored to the respective initial values on curves (54) and (64). The characteristics of the conventional sample were not restored to its initial characteristics unless it was heated to higher than 600° C., whereas the sample of the present invention was regenerated to the initial characteristics completely upon heating at 200° C. These results show that even after cyclic adsorption and desorption of water vapor (moisture), OH groups are not as firmly bonded to the element of the present invention as the conventional element, and even if OH bonding occurs, the element of the present invention can be regenerated by heating at temperatures considerably lower than are required for the conventional type. Consideration is now given as to the reason why the element of the present invention can be operated on d.c. current unlike the conventional ceramic moisture sensitive element and why it has a long service life by withstanding the bonding of OH groups. First, X-ray diffractionetry of the fired product of polymerized organic silicon compound that is the primary component of the moisture sensitive section of the element of the present invention showed that at temperatures higher than 350° C. where the organic components (e.g. methyl and phenyl groups) start to decompose and to be lost by burning, amorphous $SiO_2$ is the primary component which is crystallized slowly when the temperature exceeds 800° C.

It was also found that in this temperature range, the carbon content that remains after burning of the organic components is dispersed in the fired product. In the moisture sensitive element of the present invention, the amorphous material which is the primary component and the presence of residual carbon content contribute to increased electron conductivity and inhibited ionic conductivity, and there is little likelihood that ion polarization will occur in a static electrical field, and this is probably the reason why the element of the present invention can be used with d.c. current. The carbonaceous powder that is one of the components that make up the moisture sensitive section of the element of the present invention is added to increase this electron conductivity. Various types of carbonaceous powder are available, and when it is fired in admixture with the other components of the moisture sensitive section of the element of the present invention, the carbonaceous powder seems to be lost by burning (gasified) at a temperature which slightly differs depending upon the material but which generally is in the range of from 400° to 800° C., and evaporates from the moisture sensitive section into air. The probable reason for the high resistance of the element of the present invention to the bonding of OH groups is that first of all, the amorphous material is the primary component and secondly, at firing temperatures between 350° and 800° C., a mixture of the organic and inorganic matters which are the components that remain after decomposition of the polymerized organic silicon compound and the carbonaceous powder and silicic component is inherently incapable of causing strong chemical adsorption of moisture (water vapor) or OH groups on the surface of the moisture sensitive section.

EXAMPLE 8

Figure 15:
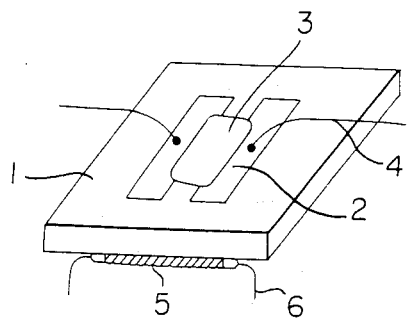
FIG. 15 is a perspective view of a moisture sensitive element according to an eighth example of the present invention.

A thinner was added to a composition having formulation 6 indicated below, and the mixture was stirred with a stirrer. The blend was applied in a thickness of about 35 μm with a brush to an alumina substrate having electrodes formed of the same material as used in Example 1, and after preliminary firing at 80° C. for 20 minutes, the assembly as fired at 450° C. for 30 minutes to cure and sinter the coat. The result was a moisture sensitive element of the present invention as shown in FIG. 15, wherein (41) is the insulation substrate, (42) is each electrode, (43) is the moisture sensitive section, (44) is each lead, (45) is a heater and (46) is a pair of leads to the heater.

| (Formulation 6) | | |
| --- | --- | --- |
| Polymerized organic silicon compound: | Methyl silicone prepolymer | 65 wt. % |
| Carbonaceous powder: | Acetylene black, graphite | 2 wt. % |
| Silicic powder: | Glass powder, ethyl silicate polymer | 28 wt. % |
| Additives: | Organoaluminum compound, MgO | 5 wt. % |

Figure 16:
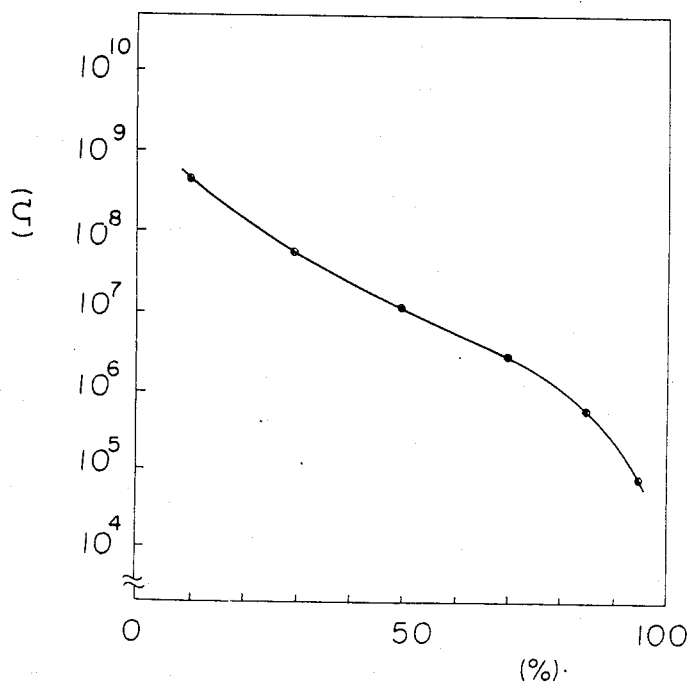
FIG. 16 is a graph showing the relative humidity vs. logarithmic electrical resistance characteristics of the moisture sensitive element according to the eighth example.
Figure 17:
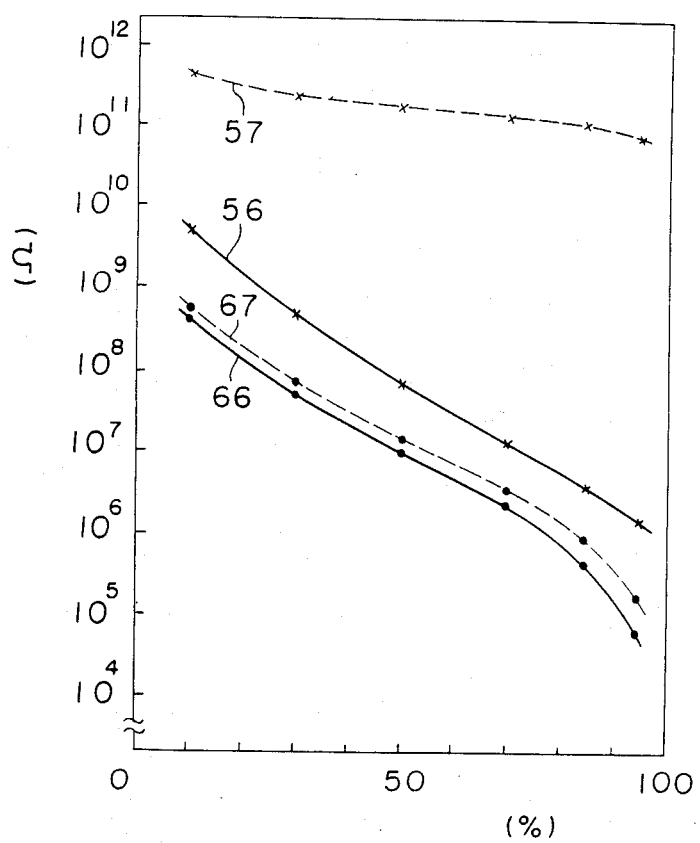
FIG. 17 is a graph showing the time-dependent relative humidity vs. logarithmic electrical resistance characteristics of a conventional moisture sensitive element and the element of the eighth example.

Two samples, the moisture sensitive element of the present invention prepared as above and a conventional ceramic sensitive element wherein the moisture sensitive section was made of $CrO_3$—MgO ceramic sintered at 1200° C. for 6 hours and the other components were the same as shown in FIG. 4, were subjected to the measurement of their moisture sensitivity characteristics and time-dependent change thereof. First, a d.c. voltage of 1 V was applied to each element as in Example 7; as soon as the voltage was applied, the resistance of the conventional type made of $CrO_3$—MgO ceramic increased to cause marked polarization. This phenomenon was more conspicuous as the fired element was left in air for a longer period. This is probably because as the adsorption of moisture in air proceeds, more of the atoms that make up the ceramic are ionized to accelerate the polarization. On the other hand, the element of the present invention fabricated as described above was entirely free of polarization upon application of d.c. current, and instead, it exhibited a gradual change in resistance and was capable of consistently measuring the change in resistance in the range of from low to high humidities as shown in FIG. 16. Then, the moisture sensitivity characteristics of the two elements and their time-dependent change were examined by applying an a.c. voltage of 1 V to the elements. To accelerate the time-dependent deterioration, the two elements were immersed in boiling water for 2 hours, and the resulting moisture sensitivity characteristics were measured for comparison with the initial characteristics. The results are shown in FIG. 17. In FIG. 17, curve (56) indicates the initial characteristics of the conventional type and curve (57) indicates the characteristics after the accelerated deterioration of the element of the present invention and curve (67) indicates the characteristics after the accelerated deterioration test. It can be seen from FIG. 17 that the values of resistance of the conventional type that had been subjected to the accelerated deterioration test were at least on hundred times as large as the initial values and its moisture sensitivity was lost completely, whereas the moisture sensitivity of the element of the present invention that had been subjected to the accelerated deterioration test was little decreased although its resistance was somewhat increased. This means the immersion in boiling water to accelerate the time-dependent deterioration was a testing method so severe as to deprive the conventional element of its ability to detect humidity, but the element of the present invention withstood this test and little deterioration occurred, so it can be said to have very high resistance to time-dependent deterioration. The element of the present invention also proved to be very strong since no signs of deterioration such as blisters or cracks were found in the moisture sensitive coat even after the test. The probable reasons for the decrease in the initial characteristics of the conventional element in the above described accelerated deterioration test are again primarily the strong chemical adsorption (bonding) of OH groups and the subsequent clogging of pores (reduction in the effective area of the moisture sensitive surface) due to the expansion of the volume of the particles in the microstructure of the ceramic. Following the accelerated deterioration test, a current was applied to the heater (see FIG. 15) on the two elements exhibiting the characteristics of curves (57) and (67) to increase their temperature from 150° C. by 50° C., and at each testing temperature, the samples were heated for 15 minutes to check the temperature at which the decreased moisture sensitivity characteristics were restored to the respective initial values on curves (56) and (66). As in Example 7, the characteristics of the conventional sample were not restored to its initial characteristics unless it was heated to higher than 600° C., whereas the sample of the present invention was regenerated to the initial characteristics completely upon heating at 250° C. which is much lower than is required for the conventional sample.

EXAMPLE 9

Moisture sensitive elements of the present invention having the constructions shown in FIGS. 12 and 15 were fabricated as in Examples 7 and 8 using compositions having formulations 7 and 8 indicated below, and their moisture sensitivity characteristics and the time-dependent change thereof were checked upon application of d.c. and a.c. currents. As a result, it turned out that, as in Example 7 and 8, the moisture sensitive element of the present invention could be operated with d.c. current and experienced little time-dependent deterioration due to bonding of OH groups. The two samples were subjected to a boiling water immersion test as in Example 8 and were found to have great strength since their moisture sensitive coat did not deteriorate at all.

| (Formulation 7) | | |
|---|---|---|
| Polymerized organic silicon compound: | Methylphenyl silicone and epoxy modified silicone prepolymers | 43 wt. % |
| Carbonaceous powder: | Carbon black, lamp black | 3 wt. % |
| Silicic powder: | Silica, colloidal silica | 38 wt. % |
| Additives: | Metal soap, TiO$_2$, bentonite | 16 wt. % |
| (Formulation 8) | | |
| Polymerized organic silicon compound: | Methylphenyl silicone prepolymer, methylmethoxysilane partial polymer | 65 wt. % |
| Carbonaceous powder: | Graphite | 10 wt. % |
| Silicic powder: | Glass powder, water glass | 16 wt. % |
| Additives: | Organic titanium compound, clay, frit | 9 wt. % |

The present inventors fabricated moisture sensitive elements using various polymerized organic silicon compounds, carbonaceous powders, amorphous silica powders and additives and by varying the proportions of the respective components, and checked their moisture sensitivity characteristics, the time-dependent change thereof and the properties of the coat in the moisture sensitive section (e.g. strength of bond to the substrate), and found that the proportions of the components must be within the following ranges. It was also found that if these ranges are not observed, the moisture sensitivity characteristics, their time-dependent change, the properties of the coat and its applicability are impaired.

| Polymerized organic silicon compound: | 20-85 wt. % |
|---|---|
| Carbonaceous powder: | 0.5-15 wt. % |
| Silicic powder: | 5-60 wt. % |

For the reasons stated above, the element is desirably fired at a temperature within the range of from 350° to 800° C., but the inventors have confirmed by experiments that practical elements can be produced even if lower or higher firing temperatures are used. As effected in the examples, the element of the present invention can be fabricated with ease and advantage by forming the moisture sensitive section in the form of a film applied from the specified composition onto an insulating substrate. If the coat thickness is too small, it has low strength and is easily affected by the characteristics of the underlying substrate, and if the coat thickness is too great, cracks may occur or the strength of bond between the substrate and the coat is decreased. It turned out that good results are obtained by limiting the coat thickness to be between 5 and 150 μm. The electrodes for detecting humidity are formed under the moisture sensitive coat (over the substrate) as shown in FIG. 1, or they may be formed on the moisture sensitive coat that has been deposited on the substrate. In the former case, high sensitivity was obtained by selecting lower values of thickness (e.g. 5-50 μm) from the above defined range of coat thickness.

According to the present invention, prepolymers of various silicon resins (including modified types) of the types described in the examples can be used as the polymerized organic silicon compound, and for example, commercial silicon varnish (prepolymers of methylphenyl silicon, etc. dissolved in solvents such as toluene and xylene) can be used with ease. As for the carbonaceous powder, those listed in the examples may be replaced by resin powders, or the product that remains after incomplete combustion of resin powders or various organic materials. As for the silicic powder, any powder of the type described in the examples that is primarily made of "silica" (SiO$_2$) can be used. Examples of such powdery material are glass, silicagel and ethyl silicate polymer, which are generally amorphous and have similar properties to those of the product that remains after burning the organic silicon compound at higher than 350° C., and this probably enhances the above described advantages of the moisture sensitive element of the present invention. But the silicic powder need not be amorphous so long as it is used together with the polymerized organic silicon compound, and experiments conducted in a similar manner to the examples confirmed that such non-armophous silicic powder could be used without greatly impairing the advantages of the element of the present invention.

INDUSTRIAL UTILITY

As described in the foregoing, the moisture sensitive element according to the present invention has a moisture sensitive section that is made of tiny particles of a moisture sensitive, electrically resistant material that are bound to each other by the product that remains after decomposing at high temperatures a composition primarily made of a polymerized organic silicon compound (silicone). Because of this feature, the element has the high sensitivity necessary for humidity detection, can measure a wide range of humidities, can be made from a cheap and easily available material and can be fabricated by a simple method. At the same time, the element has high strenght and good moisture sensitivity characteristics. What is more, it can be used for an extended period with little decrease in the moisture sensitivity characteristics and little change in the value of resistance, and even if these factors are changed, the element can be regenerated to the initial performance by heating at much lower temperatures than is required for the conventional type. As a further advantage, the element of the present invention can be fabricated by sintering at lower temperatures than has been necessary for making the conventional type and it is capable of detecting the change in relative humidity by application of d.c. current. Therefore, it can be used for an extended period as a moisture sensitive element in various devices such as humidity sensors and condensation sensors.

We claim:

1. A moisture sensitive element having a moisture sensitive section that changes its electrical resistance according to the humidity of atmosphere, said moisture sensitive section being made of a composition that contains 10 to 95 wt.% of a polymerized organic silicon compound, 5 to 90 wt.% of an amorphous silica powder and 0 to 80 wt.% of other additive components and which is sintered at a temperature higher than 300° C.

2. A moisture sensitive element comprising in sequence an electrically insulating base, a moisture sensitive section that changes its electrical resistance according to the humidity of atmosphere and a pair of electrodes formed on said moisture sensitive section, said moisture sensitive section being prepared by mixing under stirring 10 to 95 wt.% of a polymerized organic silicon compound, 5 to 90 wt.% of an amorphous silica powder and 0 to 30 wt.% of other additive components, applying a coat of the resulting blend to said base in a predetermined thickness and sintering the coat at a temperature higher than 300° C.

3. A moisture sensitive element according to claim 2 wherein the sintering at a temperature higher than 300° 1 C. is preceded by a predetermined period of preliminary firing at a temperature lower than 300° C.

4. A moisture sensitive element according to claim 2 which includes a heater for heating the moisture sensitive section.

5. A moisture sensitive element comprising in sequence an electrically insulating base, a moisture sensitive section that changes its electrical change according to the humidity of atmosphere and a pair of electrodes formed on said moisture sensitive section, said moisture sensitive section being made of a sintered product containing 20 to 85 wt.% of a polymerized organic silicon compound, 0.5 to 15 wt.% of a carbonaceous powder and 5 to 60 wt.% of a silicic powder.

6. A moisture sensitive element according to claim 5 wherein the sintering temperature is within the range of from 350° to 800° C.

7. A moisture sensitive element according to claim 5 wherein the moisture sensitive section is made of a coat having a thickness in the range of from 5 to 150 μm.

8. A moisture sensitive element according to claim 5 wherein the moisture sensitive section is prepared by mixing under stirring 20 to 85 wt.% of a polymerized organic silicon compound, 0.5 to 15 wt.% of a carbonaceous powder and 5 to 60 wt.% of a silicic powder, applying a coat of the resulting blend to said base and sintering the coat.

9. A moisture sensitive element according to claim 5 which includes a heater to heat the moisture sensitive section.

* * * * *